US009829437B2

(12) United States Patent
Chau et al.

(10) Patent No.: US 9,829,437 B2
(45) Date of Patent: Nov. 28, 2017

(54) MICROFLUIDIC BIOSENSING SYSTEM

(71) Applicant: NATIONAL CHUNG CHENG UNIVERSITY, Chia-Yi (TW)

(72) Inventors: Lai-Kwan Chau, Chiayi (TW); Hsing-Ying Lin, Kaohsiung (TW); Chen-Han Huang, Tainan (TW); Ling-Hsuan Liu, Taichung (TW); Wen-Hsin Hsieh, Taipei (TW)

(73) Assignee: NATIONAL CHUNG CHENG UNIVERSITY, Chia-Yi (TW)

( * ) Notice: Subject to any disclaimer, the term of this patent is extended or adjusted under 35 U.S.C. 154(b) by 144 days.

(21) Appl. No.: 14/714,899

(22) Filed: May 18, 2015

(65) Prior Publication Data

US 2016/0139052 A1    May 19, 2016

(30) Foreign Application Priority Data

Nov. 19, 2014  (TW) .............................. 103140133 A

(51) Int. Cl.
*G01N 21/65* (2006.01)
*B01L 3/00* (2006.01)

(52) U.S. Cl.
CPC ...... *G01N 21/658* (2013.01); *B01L 3/502761* (2013.01); *B01L 3/502715* (2013.01); *B01L 2200/0636* (2013.01); *B01L 2300/021* (2013.01); *B01L 2300/0654* (2013.01); *B01L 2300/088* (2013.01); *B01L 2300/0864* (2013.01); *B01L 2300/0867* (2013.01)

(58) Field of Classification Search
CPC ...... G01N 21/62; G01N 21/65; G01N 21/658; B01L 3/50; C12M 1/34
See application file for complete search history.

(56) References Cited

U.S. PATENT DOCUMENTS

| 2010/0177306 | A1* | 7/2010 | Natan | B82Y 30/00 356/301 |
| 2012/0123205 | A1* | 5/2012 | Nie | A61B 1/00174 600/109 |
| 2014/0094377 | A1* | 4/2014 | Ayliffe | B01L 3/502715 506/9 |

OTHER PUBLICATIONS

Pallaoro et al., Combined surface-enhanced Raman spectroscopy biotags and microflidic platform for quantitative ratiomeric discrimiation between noncancerous and cancerous cells in flow, Journal of Nanophotonics, May 9, 2013, vol. 7, pp. 1-10.*
Song et al., Continous-mode dielectrophoretic gating for highly efficient separation of analytes in surface micromachined microfluidic devices, J Micromech. Microeng. 18, 2008, pp. 1-9.*
Sebba et al., High Throughput Single Nanoparticle Spectroscopy, ACS Nano, Jun. 23, 2009; 3(6), pp. 1477-1484.*
Jun et al., Fluorescence-Based Multiplex Protein Detection Using Optically Encoded Microbeads, Molecules 2012, 17, pp. 2474-2490.*

* cited by examiner

*Primary Examiner* — Gary Counts
(74) *Attorney, Agent, or Firm* — Muncy, Geissler, Olds & Lowe, P.C.

(57) ABSTRACT

Disclosed is a microfluidic biosensing system including a processor, in which a Raman barcode database corresponding to at least one Raman spectrum signal is stored, a plurality of Raman barcode beads mixed with a target fluid and coupled to at least one target bioparticle in the target fluid, a microfluidic channel disposed to make the target fluid mixed with the Raman barcode beads flow therethrough, a light source disposed on the microfluidic channel, and a spectral detection device connected to the processor and disposed to correspond to the light source. The spectral detection device receives the Raman spectrum signal generated when the target bioparticle coupled with the Raman barcode bead is irradiated, and transfers the received Raman spectrum signal to the processor. The processor determines a type of the bioparticle(s) and calculates the number of bioparticle(s) by matching the Raman spectrum signal(s) to the Raman barcode database.

7 Claims, 13 Drawing Sheets

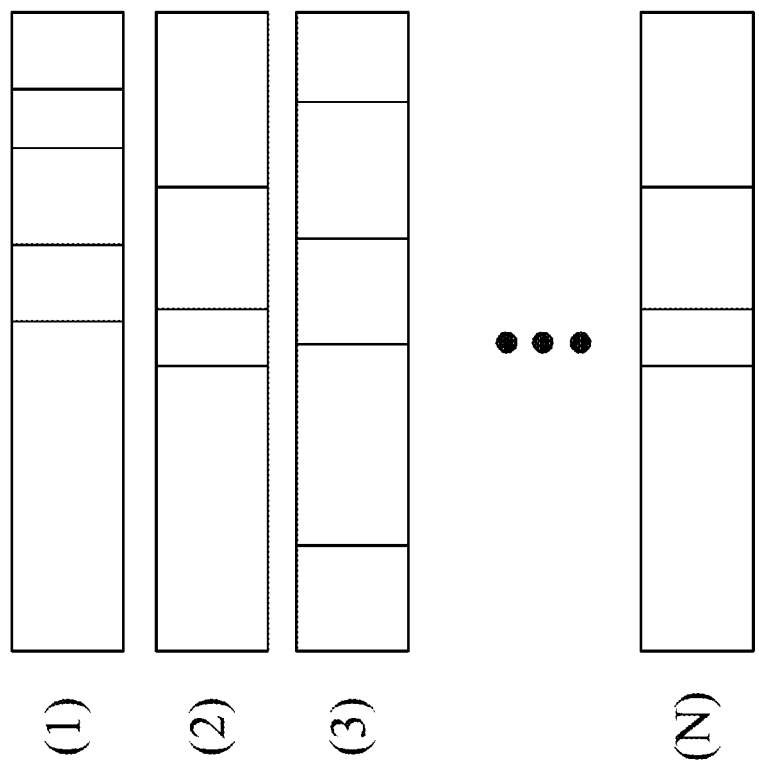

MICROFLUIDIC BIOSENSING SYSTEM

CROSS-REFERENCE TO RELATED APPLICATION

This application claims priority from Taiwan Patent Application No. 103140133, filed on Nov. 19, 2014, in the Taiwan Intellectual Property Office, the content of which are hereby incorporated by reference in their entirety for all purposes.

BACKGROUND OF THE INVENTION

1. Field of the Invention

This application relates to a microfluidic biosensing system, and more particularly, to a microfluidic biosensing system using the Raman barcode bead to sense the specific target bioparticle.

2. Description of the Related Art

When biological particles such as bacteria, viruses, cells, particles, and so on in a fluid are detected, the conventional methods often use a fluorescent label to detect the fluorescence intensity thereof. That is to say, the fluorescent label is irradiated by light after it is attached to the target bioparticle in order to confirm the presence of the target bioparticle. Because different fluorescent labels have different spectra, the fluorescent signal has been widely used in the optical barcode and the spectral labeling system. In fact, the fluorescent labels are of a wider application. For example, the fluorescent labels can be applied to the biotechnology, such as the deoxyribonucleic acid (DNA) sequencing, the DNA microarray and the fluorescent probes for the specific ions within living cells, in order to observe the physiological state, the activity, and so on of the cell.

However, after cycles of repeated exposure, the fluorescent label may encounter the technical problem such as the photo-bleaching in sensing. That is, a fluorescent label may be damaged after repeated exposure, resulting in the observation difficulties. Peak overlapping is another serious problem in terms of the fluorescent label, which leads to the errors in the observation due to the difficulties of distinguishing different fluorescent signals from each other. In addition, the fluorescent labels require a variety of excitation lights when applied to a multiplex sensing stage, so that the complexity of the whole system is raised and the increase of the overall costs becomes inevitable.

Generally, the traditional detection methods have low sensing sensitivity, need a large volume of sample, or require complex culture and testing procedures. Beside, in order to meet the requirement, the detection process often has to be performed in a particular laboratory, and usually takes a few days to weeks. As a result, the traditional detection method cannot satisfy the need for immediate multiplex detection or rapid on-site detection.

SUMMARY OF THE INVENTION

In view of the aforementioned technical problems, the objective of the present invention is to provide a microfluidic biosensing system for immediate multiplex detection or rapid on-site detection, which is not only able to detect the various target bioparticles in the target fluid, but also with the accuracy.

According to one objective of the present invention, a microfluidic biosensing system is disclosed, which may include a processor, in which a Raman barcode database corresponding to at least one Raman spectrum signal is stored, a plurality of Raman barcode beads mixed with a target fluid and coupled to at least one target bioparticle in the target fluid, a microfluidic channel disposed to make the target fluid mixed with the Raman barcode beads flow therethrough, a light source disposed on the microfluidic channel, and a spectral detection device connected to the processor and disposed to correspond to the light source. The spectral detection device receives the Raman spectrum signal generated when the target bioparticle coupled with the Raman barcode bead is irradiated by the light generated from the light source, and transfers the received Raman spectrum signal to the processor. The processor may determine a type of the bioparticle(s) and calculates a number of the bioparticle(s) by matching the Raman spectrum signal(s) to the Raman barcode database.

Preferably, the at least one Raman barcode bead may include a Raman reporter, a Raman enhancer coupled to the Raman reporter, a protective shell covering the Raman reporter and the Raman enhancer, and a biorecognition element disposed outside the protective shell. The biorecognition may correspond to the at least one target bioparticle to couple the at least one Raman barcode bead to the at least one target bioparticle. Preferably, the Raman enhancer may be metal and the metal preferably is Au or Ag.

Preferably, the Raman enhancer may be a single metal nanoparticle or a nanoaggregate of metal nanoparticles. The shape of the metal nanoparticle may be spherical, spheroid, cubic, rod, dumbbell, dog bone, polyhedron, plate, or multipods, and so on.

Preferably, an optical intensity threshold value may be set in the spectral detection device, and the at least one Raman spectrum may be valid only when an optical intensity of the at least one Raman spectrum signal at a predetermined wavenumber is greater than the optical intensity threshold value.

Preferably, the microfluidic biosensing system may further include a sheath flow channel, disposed on the microfluidic channel and providing a sheath flow to the target fluid mixed with the Raman barcode bead in advance of the target fluid being irradiated by the light generated from the light source.

Preferably, the microfluidic biosensing system may further include a light intensity detector, connected to the processor and disposed corresponding to the light source, where the light intensity detector receives an elastic scattering light signal generated when the at least one target bioparticle of the target fluid is irradiated by the light generated from the light source, and transfers the received elastic scattering light signal to the processor. The processor may determine a passing timing of the at least one target bioparticle. The passing time is when the at least one target bioparticle is irradiated by the light generated from the light source according to the elastic scattering light signal.

Preferably, the microfluidic biosensing system may further include a microelectrode set. The microelectrode set may be disposed corresponding to the light source to generate an electric field to capture the at least one target bioparticle when the at least one target bioparticle is irradiated by the light generated from the light source.

Preferably, the microfluidic flow channel may be split into a first split channel and a second split channel at one end of the microfluidic flow channel, and the microfluidic biosensing system may further include a microelectrode set. The microelectrode set is disposed where the microfluidic flow channel is split and connected to the processor, where the processor controls the microelectrode set to generated an electric field to guide the at least one target bioparticle to move toward the first split channel or the second split channel.

Preferably, the light source and the spectral detection device may be disposed relatively before the microelectrode set in a flow direction of the target fluid.

Preferably, the microelectrode set may be disposed on the first split channel.

According to the preceding description, a microfluidic biosensing system of the present invention may have one or more advantages as follows.

1. A microfluidic biological sensing system in accordance with the present invention is able to compare the Raman spectrum signals provided by the Raman barcode bead corresponding to the different target bioparticles with the Raman barcode database, such that the type and quantity of different target bioparticles can be determined so as to be applied to the analysis on the multiplex sensing stage.

2. A microfluidic biological sensing system in accordance with the present invention is able to apply the sheath flow or microelectrode set to concentrate and classify the target bioparticle in the target fluid.

3. A microfluidic biological sensing system in accordance with the present invention is able to utilize the Raman spectrum signals provided by the Raman barcode bead as a main signal source to avoid the technical problems such as the photo-bleaching effect and peak overlapping and so on, which occur when the fluorescent molecules are applied to sensing. In addition, the multiple light sources for the fluorescent labels to perform the multiplex sensing are unnecessary.

4. A microfluidic biological sensing system in accordance with the present invention is able to sense and analyze the elastic scattering light, and determine the passing timings of the target bioparticles or the other particles in the fluid.

5. A microfluidic biological sensing system in accordance with the present invention is able to utilize the different dielectrophoretic properties of different target bioparticles to capture or screen the target bioparticles by the microelectrode set.

BRIEF DESCRIPTION OF THE DRAWINGS

Hereinafter, embodiments of the present invention will be described in detail with reference to the accompanying drawings so that those skilled in the art to which the present invention pertains can realize the present invention, wherein:

FIG. 5B is a schematic diagram showing the Raman barcode obtained by analyzing the Raman spectrum signal when a microfluidic biosensing system in accordance with the present invention shown in FIG. 1 is sensing signals.

DETAILED DESCRIPTION OF THE PREFERRED EMBODIMENTS

Figure 1:
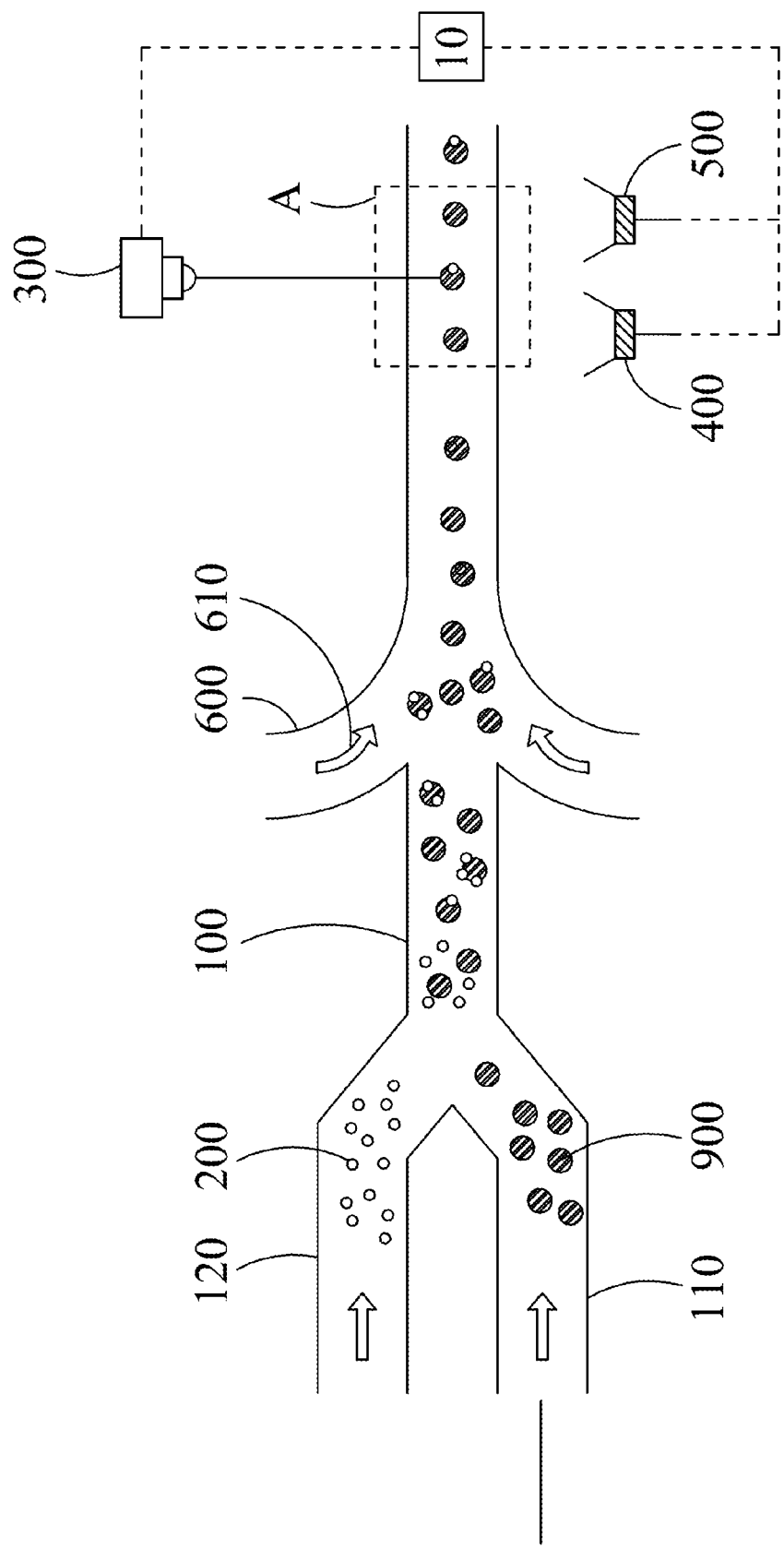
FIG. 1 is a schematic diagram of the first embodiment of a microfluidic biosensing system in accordance with the present invention.

Hereinafter, embodiments of the present invention will be described in detail with reference to the accompanying drawings so that those skilled in the art to which the present invention pertains can realize the present invention. As those skilled in the art would realize, the described embodiments may be modified in various different ways, all without departing from the spirit or scope of the present invention.

The drawings and description are to be regarded as illustrative in nature and not restrictive. Similar reference numerals designate similar elements throughout the specification.

Please refer to FIG. 1, which is a schematic diagram of the first embodiment of a microfluidic biosensing system in accordance with the present invention. In FIG. 1, a microfluidic biosensing system includes a processor 10, a plurality of Raman barcode beads 200, a microfluidic channel 100, a light source 300, and a spectral detection device 400. The processor 10 stores a Raman barcode database corresponding to at least one Raman spectrum signal. The plurality of Raman barcode beads 200 are mixed with a target fluid and coupled to at least one target bioparticle 900 in the target fluid. The microfluidic channel 100 is configured to make the target fluid mixed with the plurality of Raman barcode beads 200 to flow therethrough. The light source 300 is disposed on the microfluidic channel 100. The spectral detection device 400 is connected to the processor 10 and disposed corresponding to the light source 300, where the spectral detection device 400 receives the at least one Raman spectrum signal generated when the at least one target bioparticle 900 coupled with the Raman barcode beads 200 is irradiated by a light generated from the light source 300, and transfers the received at least one Raman spectrum signal to the processor 10. The processor 10 determines a type or types of the at least one target bioparticle 900 by matching the at least one Raman spectrum signals to the Raman barcode database, and calculates a number of the at least one bioparticle 900 of each type according to determination results of each time the Raman barcode spectrum signal is received and transferred by the spectral detection device 400. The processor 10 may be a computer or a server with calculating functions, or the like.

Specifically, the present invention applies the Raman barcode bead 200 mixed with the target bioparticle to detect the presence of the target bioparticle 900. Firstly, the frond end (the end where the fluid flows in) of the microfluidic channel is split into a first convergence channel 110 and a second convergence channel 120, where the target fluid having the target bioparticle 900 and the Raman barcode bead 200 may respectively flow therein, and be mixed in the microfluidic channel 100. Upon mixing, the Raman barcode bead 200 is bound to the target bioparticle 900 correspondingly and the binding process will be described in detail hereinafter. When the target bioparticle 900 mixed with the Raman barcode bead 200 passes through the detection area A, the light emitted from the light source 300 may shine on the target bioparticle 900 bound with the Raman barcode bead 200. The Raman barcode bead 200 has the molecules with strong Raman scattering which are called the Raman reporter 210. When the Raman reporter 210 is irradiated by light, it may be excited to produce the Raman scattering, that is, the Raman spectrum signal mentioned herein. The Raman spectrum signal may be detected by the spectral detection device 400 disposed correspondingly to the light source 300. Afterwards, the spectral detection device 400 transfers the received Raman spectrum signal to the processor 10, and the processor 10 analyzes the Raman spectrum signal. The processor 10 converts the Raman spectrum signal to a Raman barcode, and then matches the Raman barcode with the stored Raman barcode database. If there is the corresponding Raman barcode in the Raman barcode database, it means that the specific Raman barcode bead 200 is in the detection area A. Because the specific Raman barcode bead 200 may be bound to the specific target bioparticle 900, the presence of the specific target bioparticle 900 in the detection area A can be confirmed by analyzing the Raman spectrum signal. If it is known that which target bioparticle the Raman barcode bead 200 may be bound to, the type of the target bioparticle 900 can be thereby confirmed. Further, it can be confirmed when the target bioparticle 900 flows through the detection are according to the timing when the Raman spectrum signal is sensed. Hence, the amount or concentration of the target bioparticle 900 in the target fluid can be estimated. It should be noted that only one type of the target bioparticle 900 is shown in FIG. 1 seemingly, but a microfluidic biosensing system in accordance with the present invention is able to simultaneously sense and count the presence of different target bioparticles, that is, the multiplex sensing and analyzing can be made. To achieve this objective, it only needs to prepare different Raman barcode beads according to the types of the target bioparticles, and to enable the different Raman barcode beads to bind to the different target bioparticles. Because the Raman reporter in the Raman barcode bead can be determined freely according to the actual requirement and the different Raman reporters emit the different Raman spectrum signals, the different Raman barcode beads passing through the detection area A can be confirmed by analyzing the different Raman spectrum signals. That is, it can be found that the different target bioparticles bound to the different Raman barcode beads pass through the detection area A.

In the above description, the light source 300 may be a laser, and thus it may have a characteristic of a highly focused light beam. That is to say, the detection area A, where the target bioparticle 900 bound with the Raman barcode bead 200 is irradiated by the light, may become smaller, such that the location of the target bioparticle 900 may be determined more precisely and the counting result thereby becomes more accurate. In addition, the type of the laser can be determined according to the type of the Raman barcode bead 200, or the Raman reporter 210 in the Raman barcode particle 200.

In the case that the target bioparticles are bacteria, cells, viruses, particles, etc., the size of the microfluidic channel 100 may be in the micron scale, and the other units such as the light source 300 and the spectral detection device 400 may be arranged in the micron scale correspondingly. Therefore, the above-mentioned system can be integrated as a whole in a biological detection chip, and is portable and able to perform the rapid on-site detection. Further, since a microfluidic biosensing system in accordance with the present invention also has the detection capability in the micron scale, it is possible to effectively reduce the amount of sample used for sensing.

Figure 2:
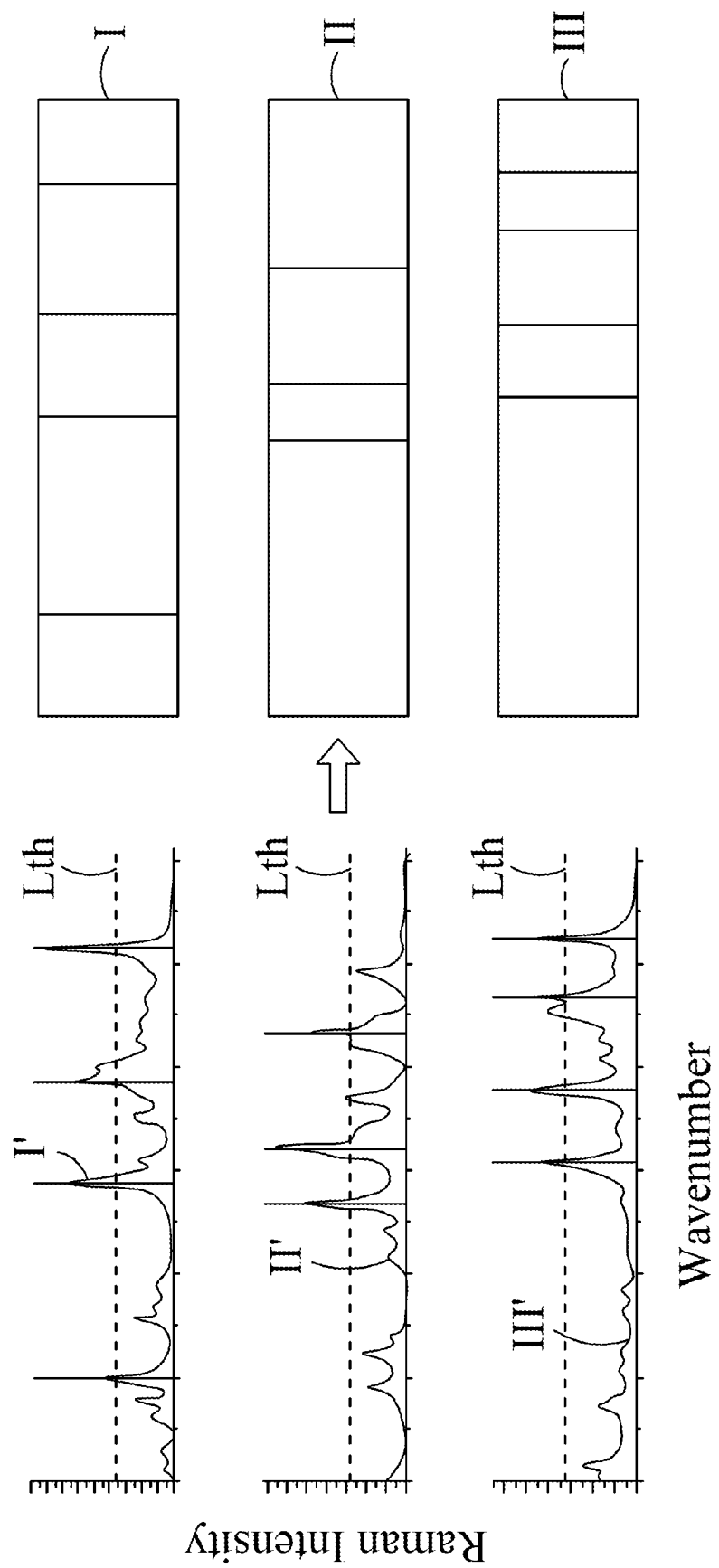
FIG. 2 is a schematic diagram showing the Raman spectrum signal of a microfluidic biosensing system in accordance with the present invention being transferred into the Raman tag barcode.

Please refer to FIG. 2, which is a schematic diagram showing how the Raman spectrum signals I', II', III' of a microfluidic biosensing system in accordance with the present invention are transferred into the Raman tag barcodes I', II', III'. In FIG. 2, the spectral detection device 400 may include an optical threshold value $L_{th}$, and when the optical intensity values (i.e. the Raman spectrum intensity value shown in FIG. 2) of the specific wavenumbers of the Raman spectrum signals I', II', III' exceed the optical threshold value $L_{th}$, the signals are considered as the valid signals.

Specifically, as shown in left of FIG. 2, when the Raman barcode bead 200 is irradiated by the light emitted from the light source 300, the Raman spectrum signal is generated. In FIG. 2, the characteristic of the Raman spectrum signals I', II', III' may be defined by the peak value of the Raman spectrum intensity. Therefore, the optical threshold value $L_{th}$ may further be set in the spectral detection device 400. When the spectrum intensity of the wavenumbers of the peak values of the Raman spectrum signals I', II', III' exceeds the optical threshold value $L_{th}$, the signals are considered as valid and are read by the spectral detection device 400. After the spectral detection device 400 reads the Raman spectrum signals I', II', III', the Raman spectrum signals I', II', III' can be converted into the Raman barcodes I, II, III as shown in right of FIG. 2. Afterwards, the processor matches the Raman barcodes I, II, III with the data in the Raman barcode database to confirm whether the specific Raman barcode bead 200 exists in the detection area A. What has to be addressed is that only three types of the Raman spectrum signals are shown in FIG. 2, the amount and type of the Raman barcode bead 200, however, may be selected freely according to the detection. In addition, the setting of the optical threshold value $L_{th}$ may be adjusted freely based on the actual requirement such that the different Raman spectrum signals emitted by different Raman barcode beads 200 can be differentiated. On the other hand, the setting of the optical threshold value $L_{th}$ can prevent the detection device 400 from receiving the background noise and misjudging it as the valid Raman spectrum signal. In addition, as the emitted Raman spectrum signal is weaker when just the Raman barcode bead 200 flows through the detection area A without binding to the target bioparticle 900, the optical threshold value $L_{th}$ may be set to filter such signals so as to prevent making the misjudgments that the target bioparticle 900 exist in the detection area A.

Figure 3A:
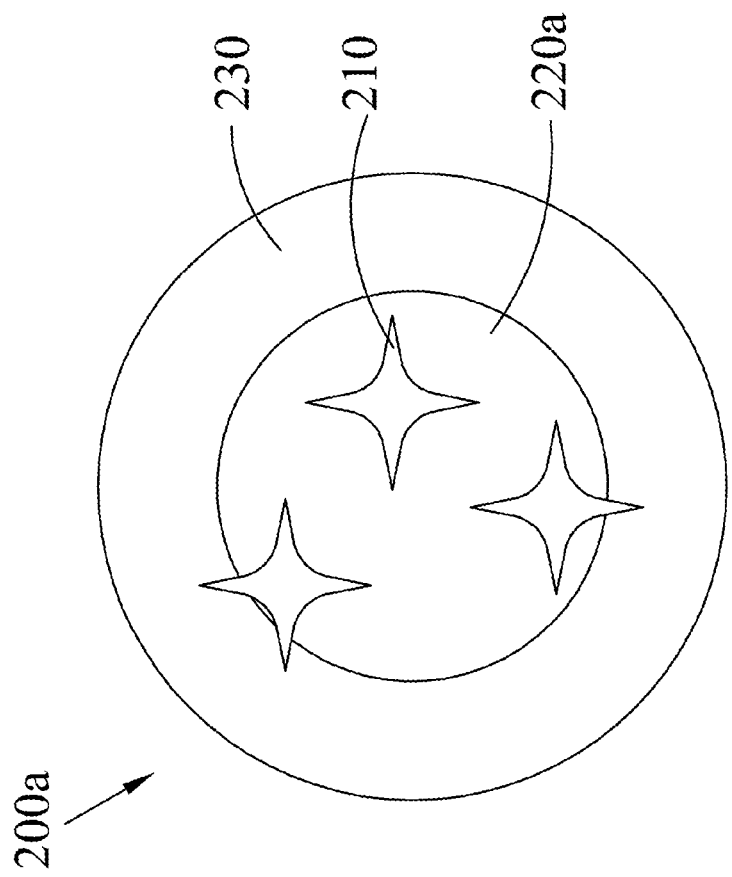
FIG. 3A to FIG. 3C are the schematic diagrams showing embodiments of the formation of the Raman barcode beads in accordance with the present invention.
Figure 3B:
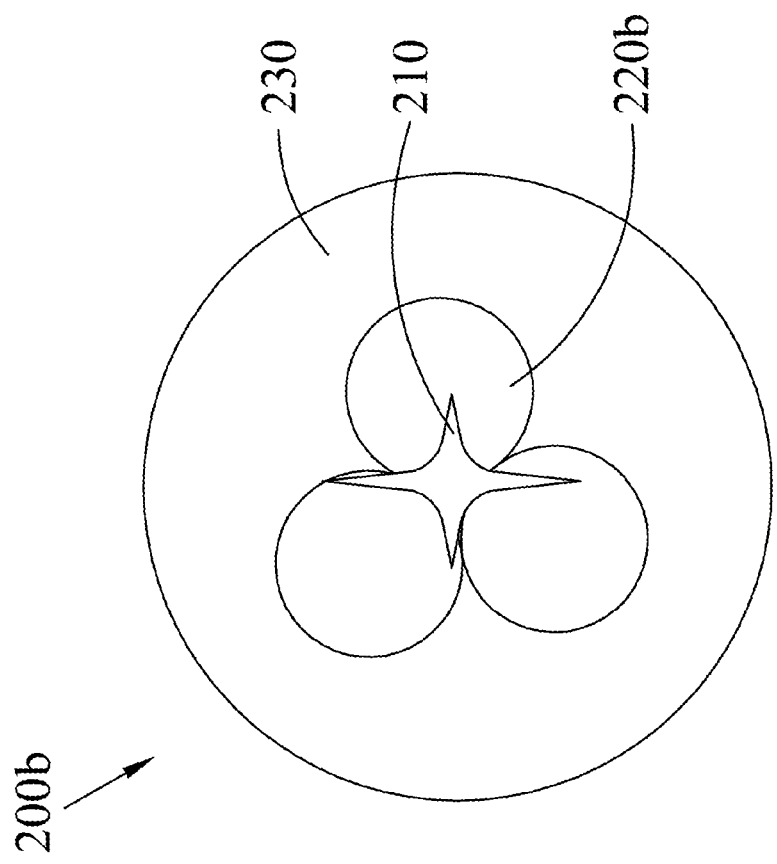
Figure 3C:
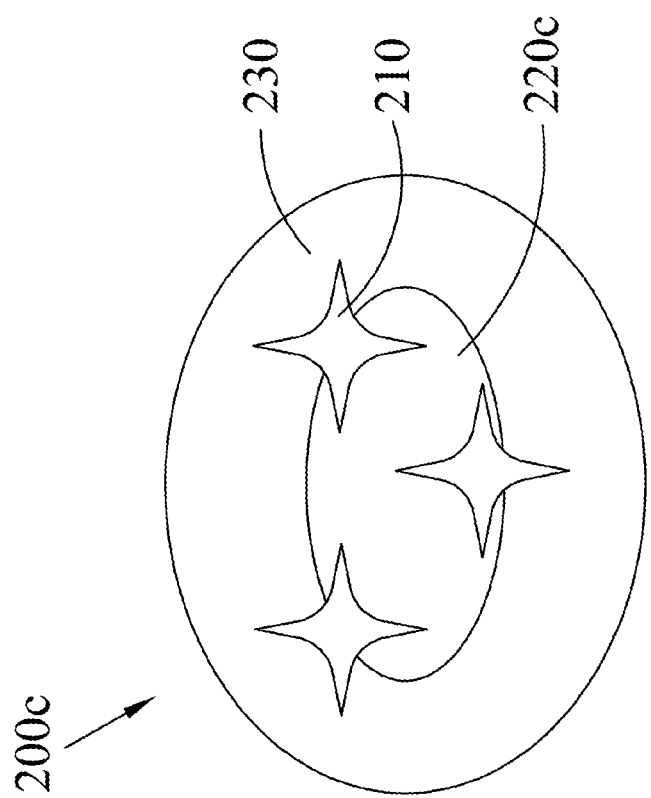

Please refer to FIG. 3A to FIG. 3C which are the schematic diagrams showing an embodiment of the formation of the Raman barcode beads 200 in accordance with the present invention. In the figures, the Raman barcode beads 200 may include the Raman enhancer, the Raman reporters 210 bound to the Raman enhancer, the protective shell 210 covering the Raman reporters 210 and the Raman enhancer. The Raman enhancer may be a single spherical metal nanoparticle 220a (as shown in FIG. 3A), a nanoaggregate 220b (as shown in FIG. 3B), or a single rod-shape metal nanoparticle 220c (as shown in FIG. 3C). The nanoaggregate is preferred.

In particular, the different Raman reporters 210 have different Raman scattering spectra, and thus, they may produce the different Raman spectrum signals. The different Raman spectrum signals may correspond to the different Raman barcodes when the different Raman reporters 210 are irradiated by lights. Since the types of the Raman reporters 210 are selected freely, the generated Raman barcode is known. These produced Raman barcodes are served as the sources of the Raman barcode database stored in the processor 10. However, at the time of detection, if the Raman barcode bead 200 only contains the Raman reporter 210, the Raman scattering light excited by the light becomes too weak and leads to the difficulty of the detection. Therefore, in practice, when the Raman barcode bead 200 is produced, the Raman reporter 210 is bound to the Raman enhancer, such that the Raman enhancer excited by light is able to produce the surface enhancement effect so as to reinforce the local electric field and obtain the optical gain of emitted Raman spectrum signal of the Raman reporter 210. Such spectrum obtaining the optical gain via the surface enhancement effect is also called the surface-enhanced Raman scattering (SERS) spectrum of the Raman reporter 210. As mentioned above, the use of Raman enhancer can have a variety of choices. Please refer to FIG. 3A. In the Raman barcode bead 200a, the used Raman enhancer may be the single spherical metal nanoparticle 220a, and the single spherical metal nanoparticle 220a may be directly obtained from the market or prepared by the conventional method, such that the production process can be simplified and the production cost of the Raman barcode bead 200a can be reduced. Alternately, please refer to FIG. 3B. In the Raman barcode bead 200b, the used Raman enhancer may be the nanoaggregate 200b. The hot spot may be produced in the interstitial sites of the nanoaggregate 200b, so as to provide considerable optical gain to the Raman spectrum signal to highly enhance the intensity of the emitted Raman spectrum signal. Please refer to FIG. 3C. In the Raman barcode bead 200c, the used Raman enhancer may be the single rod-shape metal nanoparticle 200c, and the aspect ratio of the rod-shape metal nanoparticle 200c may be selected freely according to the actual requirement. For example, the aspect ratio between a long axis and a short axis of the rod-shape nanoparticle 200c may be changed to correspond to the different plasmon resonance bands. Hence, the single rod-shape metal nanoparticle 200c is used to provide the Raman spectrum signals in longer-wavelength region such as the near infrared region to resonate, so as to provide the Raman spectrum signal in the longer-wavelength region with the necessary optical gain.

The protective shell 230 may cover the Raman reporter 210 and the Raman enhancer when the Raman reporter 210 binds the Raman enhancer. The material of the protective shell 230 may be selected specifically, such as silica or a metal oxide, so as to increase the biocompatibility and avoid the non-specific adsorption, which may alter the Raman spectrum signal of the Raman barcode bead 200. Preferably, the material of the protective shell 230 is silica. On the other hand, the protective shell 230 may prevent the bound Raman reporter 210 leaking from the bead, where such leaking may disable barcoding function of the Raman barcode bead 200.

Figure 4:
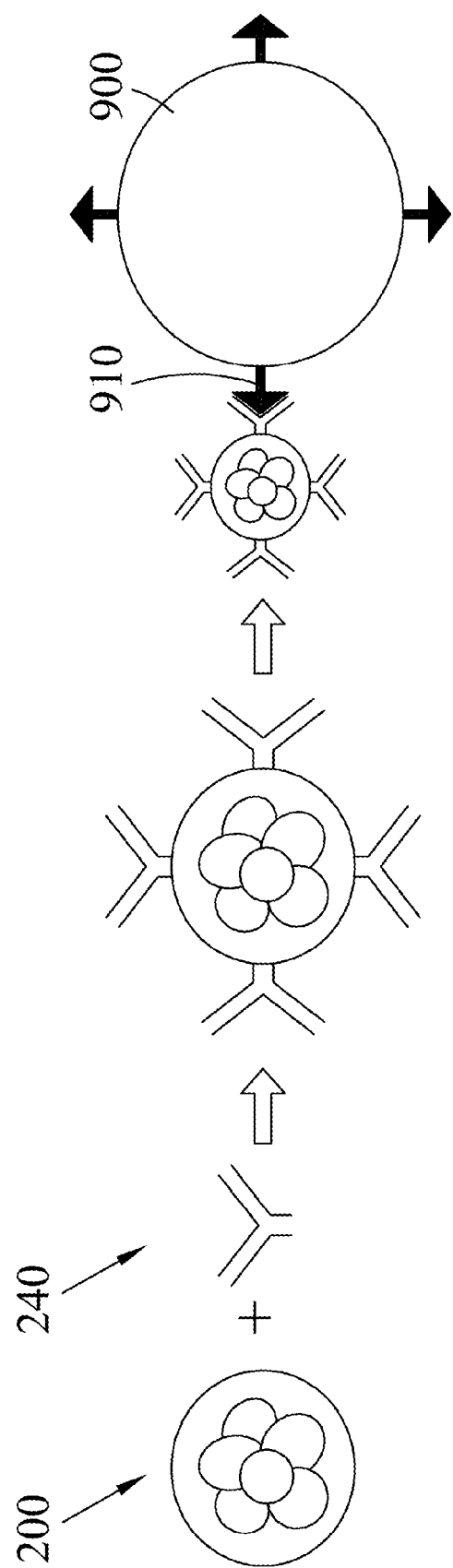
FIG. 4 is a schematic diagram showing how the Raman barcode bead of the present invention is combined with the biorecognition elements and then binds with the target bioparticles.

Please refer to FIG. 4 which is a schematic diagram showing how the Raman barcode bead of the present invention is combined with the biorecognition element in order to bind with the target bioparticles. In FIG. 4, a biorecognition element 240 may be disposed on the outer surface of the protective shell 230, where the biorecognition element 240 corresponds to the target bioparticle 900, such that the Raman barcode bead 200 is able to bind with the target bioparticle 900.

The established structures of the Raman barcode beads 200 can be referred to FIG. 3A to FIG. 3C, and then please refer to FIG. 4. The biorecognition element 240 may be disposed on the outer surface of the protective shell 230. The type of the biorecognition element 240 is selected according to the desired target bioparticle 900. The biorecognition element 240 may be an antigen, an antibody, a nucleic acid, a lectin, a hormone receptor, a saccharide, and the like. For example, as shown in FIG. 4, the biorecognition element 240 bound to the outer surface of the Raman barcode bead 200 may be an antibody, and the outer surface of the target bioparticle 900 has the antigen 910 corresponding to the antibody. Thus, by immobilization of the specific biorecognition element 240 on the outer surface of the Raman barcode bead 200, the Raman barcode bead 200 is able to bind with the specific target bioparticle 900 in the target fluid when the Raman barcode bead 200 is mixed with the target fluid.

In summary, the produced and to-be-used Raman barcode bead 200 may include the Raman reporter 210, the Raman enhancer, the protective shell 230 and the biorecognition element 240. Structure of such Raman barcode bead 200 is able to provide a microfluidic biosensing system in accordance with the present invention with the better characteristics of the biostability, biological compatibility and specific binding for biolabeling and biosensing.

Please refer to FIG. 1. In FIG. 1, a microfluidic biosensing system in accordance with the present invention includes a sheath flow channel 600 disposed on the microfluidic channel 600 and providing a sheath flow 610 to the target fluid mixed with the Raman barcode bead 200 in advance of the target fluid being irradiated by the light generated from the light source 300.

In order to improve the accuracy of detection, it is desirable to make the target bioparticle 900 in the target fluid pass through the detection area A in sequence. That is, the target bioparticles 900 in the target fluid enter the detection area A one by one. In order to achieve this objective, a microfluidic biosensing system in accordance with the present invention further includes the microfluidic channel 600 on the microfluidic channel. The microfluidic channel 600 provides the sheath flow 610 with the target fluid before the target fluid mixed with the Raman barcode bead 200 flows through the detection area A, such that the target bioparticles 900 in the target fluid are focused so as to achieve the aforementioned "flow in sequence". It is worth mentioning that the shapes of the microfluidic channel and the other channels disclosed in a microfluidic biosensing system in accordance with the present invention are not limited thereto. The microfluidic channel for other functions may be produced according to the actual requirement. For example, a microfluidic biosensing system in accordance with the present invention may further include an additional convergence channel which facilitates various fluids to be mixed, or the split channel may be included for facilitating the fluids flowing therethrough to perform further screening. The various embodiments of screening the target fluids may be detailed in the following paragraphs.

Please refer to FIG. 1. In FIG. 1, a microfluidic biosensing system in accordance with the present invention may further include a light intensity detector 500 connected to the processor 10 and disposed corresponding to the light source 300, where the light intensity detector 500 receives an elastic scattering light signal generated when the at least one target bioparticle 900 of the target fluid is irradiated by the light generated from the light source 300, and transfers the received elastic scattering light signal to the processor 10. The processor 10 determines a passing timing when the target bioparticle 900 is irradiated by the light generated from the light source according to the elastic scattering light signal.

In the practical detection, when the light source 300 shine the light on the target bioparticle 900 bound with the Raman barcode bead 200, the excited scattering light includes elastic scattering light and the Raman scattering light. The Raman scattering light is the aforementioned Raman spectrum signal. Hence, a microfluidic biosensing system in accordance with the present invention may further include the light intensity detector 500 used to receive the elastic scattering light and transmit the elastic scattering light to the processor 10 simultaneously when performing the detection. The processor 10 may analyze the passing time of the target bioparticle 900 in the target fluid by the variety of the elastic scattering light when receiving the elastic scattering light signal. Since the size of the Raman barcode bead (nano scale) is smaller than that of the target bioparticle (micron scale), the elastic scattering light from the Raman barcode without binding to the target bioparticle is weak and of background noise level. Consequently, the measurement of the scattering light of the target bioparticle is not affected. The details are explained by the analysis obtained from both the spectral detection device 400 and the light intensity detector 500.

Figure 5A:
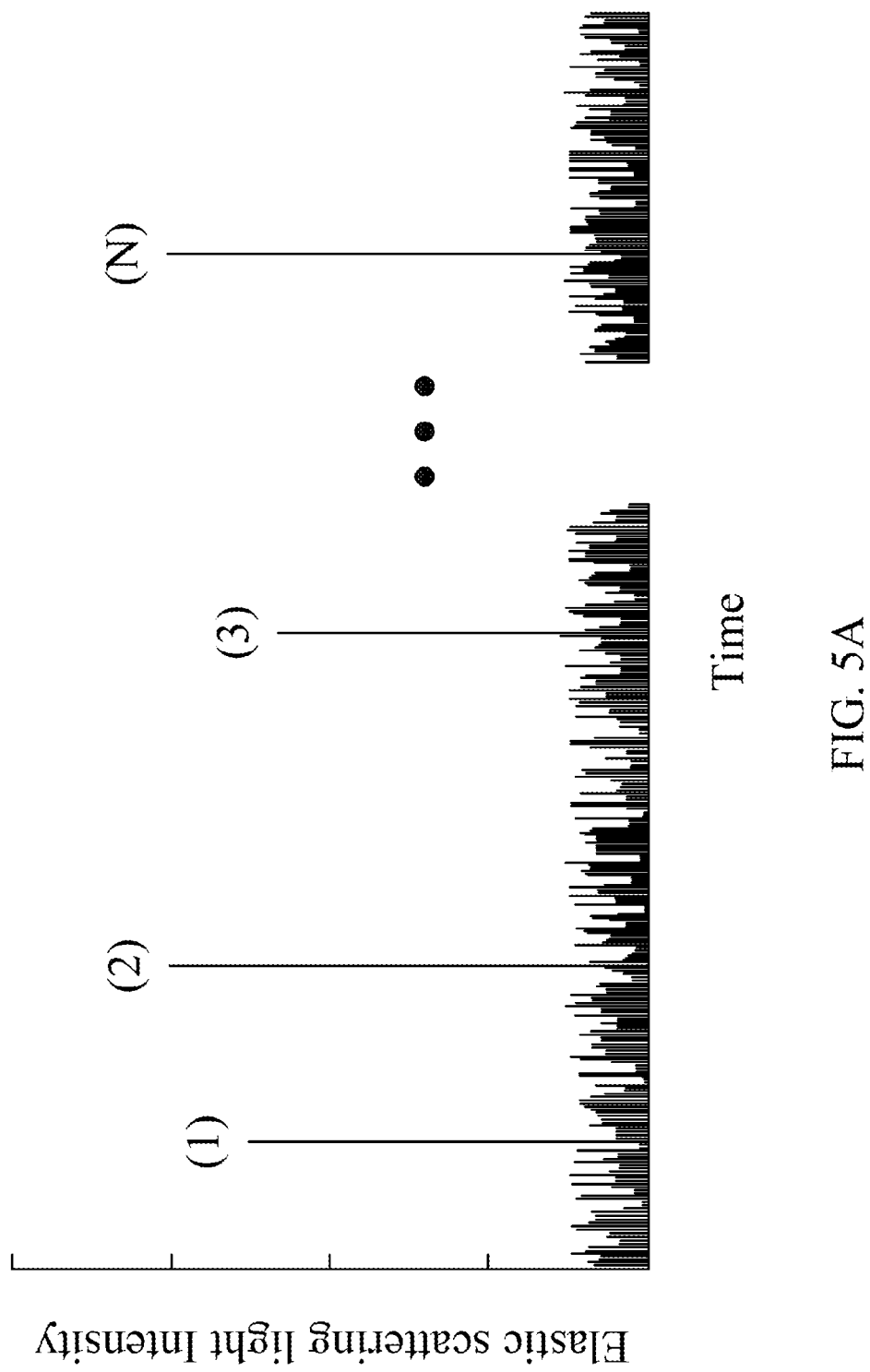
FIG. 5A is a schematic diagram showing the elastic scattering signals when a microfluidic biosensing system in accordance with the present invention shown in FIG. 1 is sensing signals.
Figure 5C:
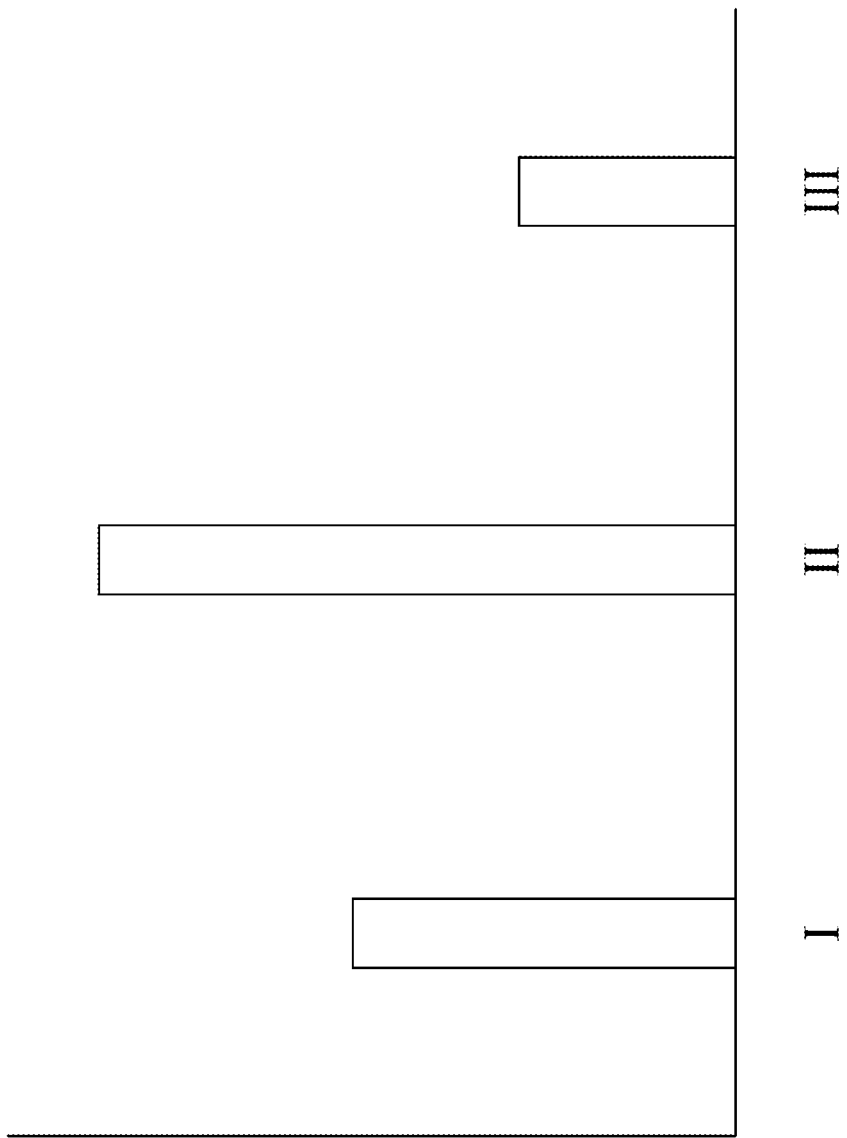
FIG. 5C is a bar chart showing different amounts of the target bioparticles obtained from the combined test results of FIG. 5A and FIG. 5B.

Please refer to FIG. 5A to FIG. 5C which are respectively a schematic diagram showing the obtained signals and the analyzed results when a microfluidic biosensing system in accordance with the present invention shown in FIG. 1 is sensing signals FIG. 5A is a schematic diagram showing the elastic scattering signals. FIG. 5B is a schematic diagram showing the Raman barcode obtained by analyzing the Raman spectrum signal. FIG. 5C is a bar chart showing different amounts of the target bioparticles obtained from the combined test results of FIG. 5A and FIG. 5B.

Specifically, when the target bioparticle 900 mixed with the Raman barcode bead 200 is flowing through the detection area A and is irradiated by the light emitted from the light source 300, the peak value of the elastic scattering light which may be detected by the light intensity detector 500 is generated. For example the peak value (1) of the elastic scattering light shown in FIG. 5A. In this case, the Raman spectrum signal is provided by the Raman barcode bead 200, and then correspondingly converted to the Raman barcode, such as the Raman barcode (1) shown in FIG. 5B. When next one target bioparticle 900 bound with the Raman barcode bead 200 is flowing through the detection area A and is irradiated by the light source 300, the peak value (2) of the scattering light shown in FIG. 5A and the Raman barcode (2) shown in FIG. 5B are produced simultaneously. When the third target bioparticle 900 bound with the Raman barcode bead 200 is flowing through the detection area A and is irradiated by the light source 300, the peak value (3) of the scattering light shown in FIG. 5A and the Raman barcode (3) shown in FIG. 5B are produced simultaneously, and the like. When the $N^{th}$ target bioparticle 900 bound with the Raman barcode bead 200 is flowing through the detection area A and is irradiated by the light emitted from the source 300, the N peak values of the scattering light and the N Raman barcodes are accumulated and recorded in the processor 10. In the sensing process, the processor 10 may simultaneously match and count the Raman barcode with the Raman barcode database. For example, as shown in FIG. 2, the processor is able to determine the Raman barcode (1) belonging to the Raman barcode III of FIG. 2, the Raman barcode (2) belonging to the Raman barcode II of FIG. 2, the Raman barcode (3) belonging to the Raman barcode I of FIG. 2, . . . and the Raman barcode ($N^{th}$) belonging to the Raman barcode II of FIG. 2. Hence, when the target fluid flows through the detection area A, the amount of each target bioparticle 900 in the target fluid can be obtained. On the other hand, if the target bioparticle 900 without being bound with the Raman barcode bead 200 flows through the detection area A, the peak value of the elastic scattering light may be detected while the Raman spectrum signal is below the optical threshold value $L_{th}$ and hence will not be counted.

On the other hand, if the binding characteristic of the surface of the target bioparticle 900 is known, but the actual size thereof remains unknown, by applying a microfluidic biosensing system in accordance with the present invention to perform the detection, the actual size of the target bioparticle can be obtained by analyzing the generated elastic scattering signal. Similarly, the Raman barcode may not be produced when the other particles different from the target bioparticle 900 in the target fluid flow through the detection area A. However, the corresponding peak value may be produced on the elastic scattering light signal, such that the size of the other particles in the target fluid and the relative proportion of the target bioparticle 900 and the other particles in the target fluid can thereby be analyzed.

Figure 6:
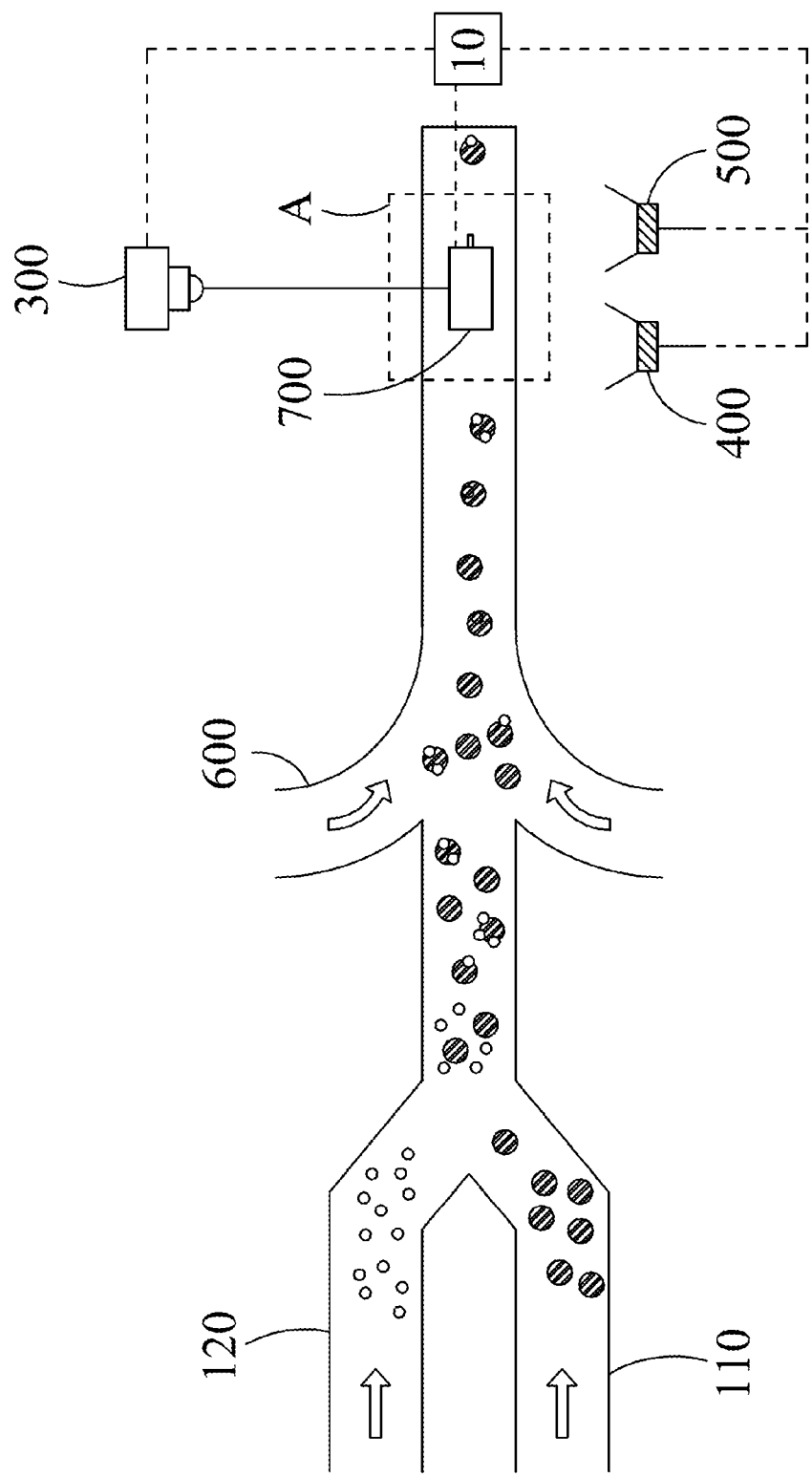
FIG. 6 is a schematic diagram of the second embodiment of a microfluidic biosensing system in accordance with the present invention.

Please refer to FIG. 6, which is a schematic diagram of the second embodiment of a microfluidic biosensing system in accordance with the present invention. In FIG. 6, a microfluidic biosensing system includes a microelectrode set 700 disposed corresponding to the light source 300 to generate an electric field to capture the target bioparticle 900 when the target bioparticle 900 is irradiated by the light generated from the light source 300.

In the first embodiment, the target fluid keeps flowing and is continuously being detected. Hence, a microfluidic biosensing system of the first embodiment may be considered as a continuous detection system. In order to further enhance the accuracy of the detection, the microelectrode set 700 can be disposed on the microfluidic channel 100 corresponding to the light source 300, and the dielectrophoresis characteristic of the target bioparticle 900 is used to capture the target bioparticle 900 as shown in the second embodiment of a microfluidic biosensing system in accordance with the present invention in FIG. 6. For example, the microelectrode set 700 is disposed in the detection area A in form of rectangular electrodes. Consequently, when the target bioparticle 900 flows through the detection area A, the microelectrode set 700 generates the electric field to capture the target bioparticle 900 in the detection area A, such that the passing time of the target bioparticle 900 in the detection area A becomes longer and hence larger signals can be obtained. Therefore, the number of the target particles 900 passing through the detection area A can be more accurately counted so as to enhance the accuracy of the detection.

Figure 7:
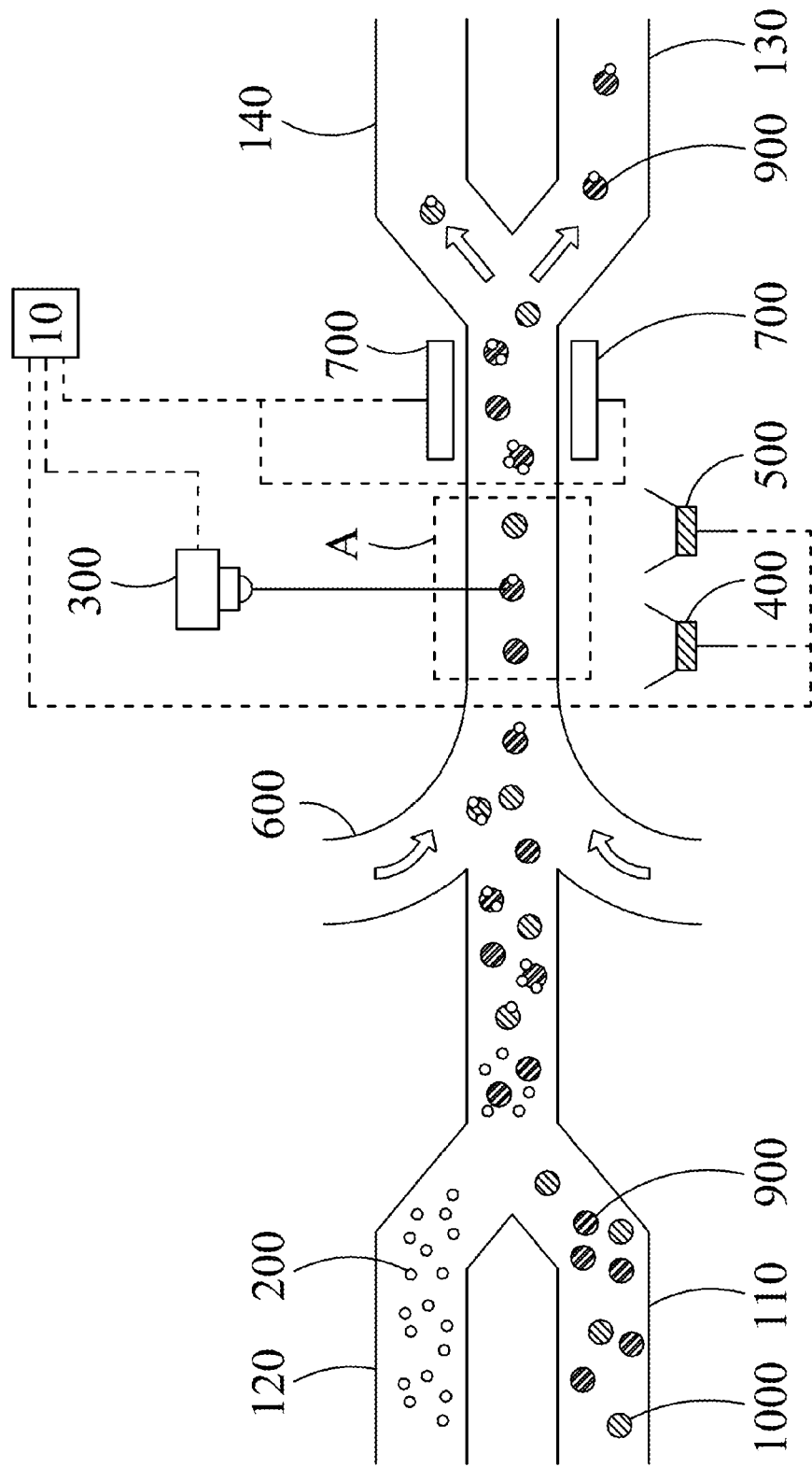
FIG. 7 is a schematic diagram of the third embodiment of a microfluidic biosensing system in accordance with the present invention.

Please refer to FIG. 7, which is a schematic diagram of the third embodiment of a microfluidic biosensing system in accordance with the present invention. In FIG. 7, the microfluidic flow channel 100 is split into a first split channel 130 and a second split channel 140 at one end of the microfluidic flow channel 100, and the microfluidic biosensing system further includes the microelectrode set 700 disposed where the microfluidic flow channel 100 is split and connected to the processor 10, where the processor 10 controls the microelectrode set 700 to generate an electric field to guide the at least one target bioparticle 900 to move toward the first split channel 130 or the second split channel 140.

In addition to capturing the bioparticle to improve the accuracy of the detection, the microelectrode set 700 can screen the target bioparticle by the dielectrophoresis characteristic of the target bioparticle 900 as well. For example, the target fluid in the third embodiment has two types of the target bioparticles 900, 1000 which respectively have different dielectrophoresis characteristics. The microfluidic flow channel 100 is split into the first split channel 130 and the second split channel 140 at the end of the microfluidic flow channel 100, and the microelectrode set 700 is disposed where the microfluidic flow channel 100 is split and connected to the processor 10, where the processor 10 controls the microelectrode set 700 to generate the electric field to guide the target bioparticles 900, 1000 to move toward the first split channel 130 or the second split channel 140 according to the dielectrophoresis characteristics of the target bioparticles 900, 1000. Furthermore, the microelectrode set 700 is configured to connect with the processor 10. As the processor 10 is able to determine which target bioparticle 900 or 1000 may flow through the microelectrode set 700 and transmit the related signals to the microelectrode set 700 according to the received result corresponding to the Raman barcode and the Raman barcode database, the electric field produced by the microelectrode set 700 may be optimized for the target bioparticle 900 or 1000 which is about to flow therethrough such that the target bioparticles 900 and 1000 are able to be separated more effectively so as to achieve the screening.

In addition, the electric field generated by the microelectrode set 700 may also be used to mix the different bioparticles or other particles. The basic principle is the same as the aforementioned screening process, which both use the electric field to guide the flowing direction according to the dielectrophoresis characteristics of the particles. Hence, the unnecessary details are no longer given herein.

Figure 8:
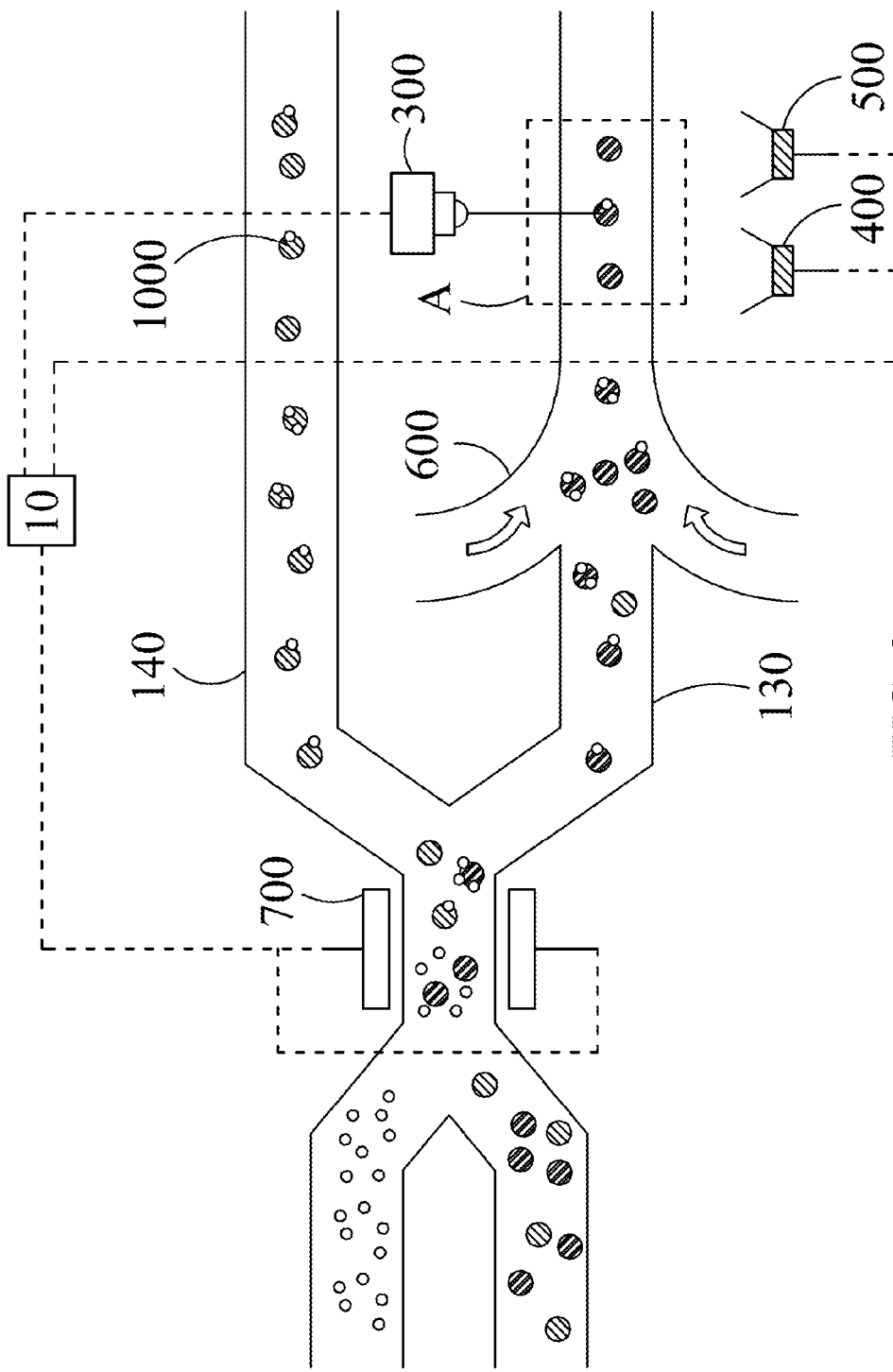
FIG. 8 is a schematic diagram of the fourth embodiment of a microfluidic biosensing system in accordance with the present invention.

Please refer to FIG. 8 which is a schematic diagram of the fourth embodiment of a microfluidic biosensing system in accordance with the present invention, wherein the forth embodiment is akin to the third embodiment. The microfluidic channel 100 is split into the first split channel 130 and the second split channel 140 at the end of the microfluidic flow channel 100, and the microelectrode set 700 is disposed where the microfluidic flow channel is split. The difference between the third and the fourth embodiments lies in that the light source 300 and the spectral detection device 400 in the fourth embodiment are disposed on the first spilt channel, and the light intensity detector 500 and the sheath flow channel 600 are disposed on the first split channel 130 correspondingly.

In the fourth embodiment, the detection result of the target bioparticles 900, 1000 may be applied to check the screening result of the target bioparticles 900, 1000 performed by the electric field generated by the microelectrode set 700. For example, in the embodiment, the detection area A formed with the light source 300, the spectral detection device 400, and so on disposed on the first split channel 130 is applied to detect the relative proportion of the target bioparticles 900, 1000 in the fluid flowing through the first split channel 130. If the relative proportion between the target bioparticles 900, 1000 is known, comparing the former and the latter relative proportion between the target bioparticles 900, 1000 may lead to the screening result of the microelectrode set 700. In addition, in the embodiment, the microelectrode set 700 may be connected to the processor 10. As the detection of the target bioparticles 900, 1000 made by a microfluidic biosensing system in accordance with the present invention is continuous, the processor 10 is able to actually calculate the instant relative proportion between the target bioparticles 900, 1000, and then transmit the related signals to the microelectrode set 700. As a result, the microelectrode set 700 may refer to the signals to adjust the electric field used to screen the target bioparticles 900, 1000, such that the optimal condition of using the microelectrode set 700 for screening can be found quickly. It is worthy to mention that the Raman barcode bead 200 has metal particle, but the size of the metal particle is in the nano scale, and the original dielectrophoresis characteristics of the target bioparticles 900, 1000 may not be affected apparently. Thus, if there are a great number of similar fluid samples to be screened, only a few fluid samples are necessary to test the optimal screening condition. Afterwards, the optimal screening condition can be used to screen the remaining fluid samples. Therefore, the consumption of the Raman barcode bead 200 can be saved greatly and the target fluids can be screened quickly and effectively so as to be provided for the next stage of the detection and analysis.

Figure 9:
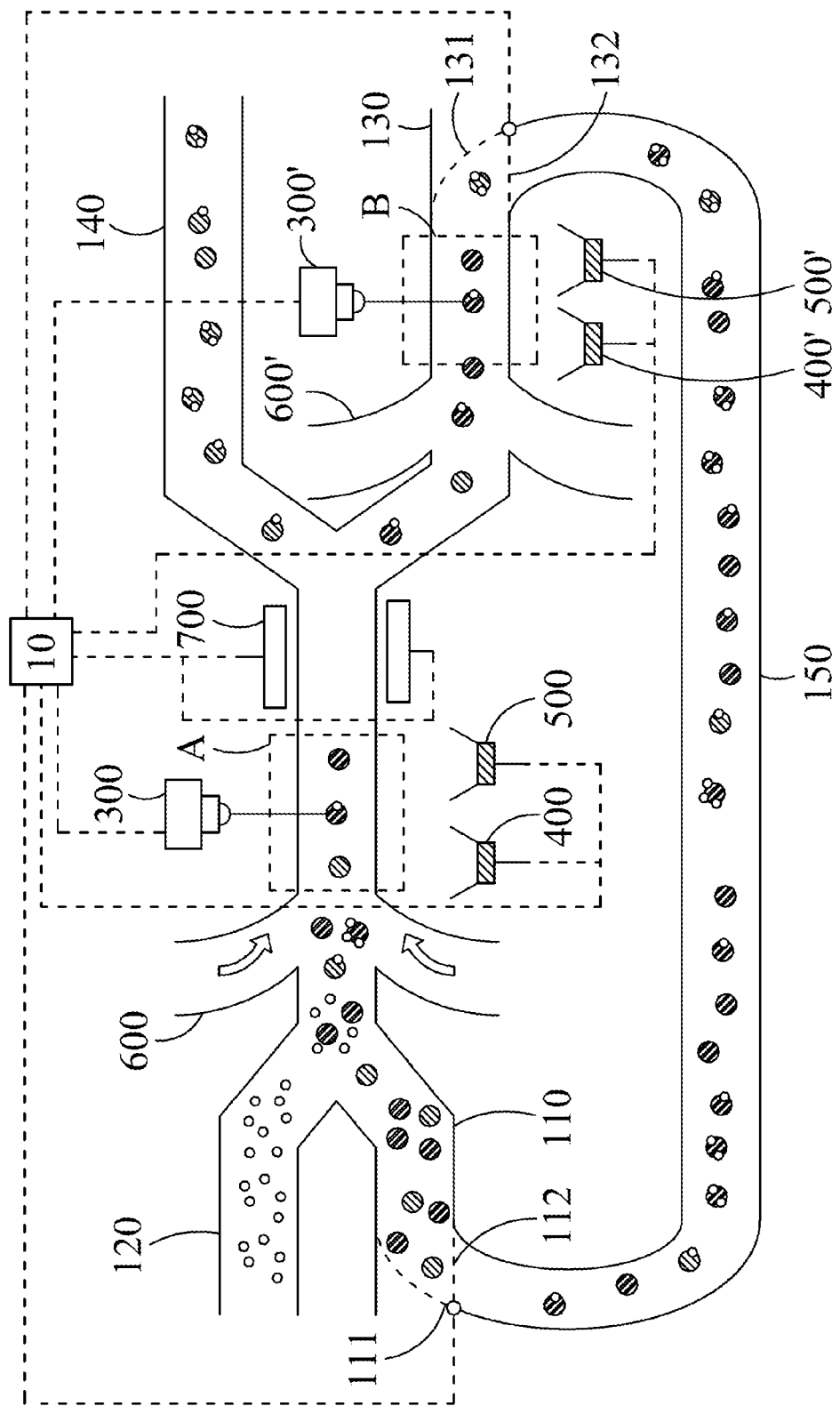
FIG. 9 is a schematic diagram of the fifth embodiment of a microfluidic biosensing system in accordance with the present invention.

Please refer to FIG. 9, which is a schematic diagram of the fifth embodiment of a microfluidic biosensing system in accordance with the present invention. Basically, the fifth embodiment combines the characteristics of the third and the fourth embodiments. The detection areas A and B are respectively disposed before and after the screening by the microelectrode set 700. The detection area A is disposed on the microfluidic channel in front of the microelectrode set 700, and the detection area B is disposed on the first split channel 130. The detection area A is formed with the light source 300, the spectral detection device 400 and the light intensity device 500. The sheath flow channel 600 is disposed in the front end of the detection area A. The detection area B is formed with the light source 300', the spectral detection device 400' and the light intensity device 500'. The sheath flow channel 600' is disposed in the front end of the detection area B. Hence, even the relative proportion between the target bioparticles 900, 1000 in the target fluid is unknown, it can be detected by analyzing the detection result of the detection area A. When the target fluid flows through the area where the microelectrode set 700 is disposed, the target fluid is screened by the electric field generated by the microelectrode set 700, and the detection result of the detection area B is used to confirm the screening result. Moreover, the first split channel 130 may be connected with the first convergence channel 110 through a connecting channel 150, and valves 111, 112, 131, 132 controlled by the processor 10 are disposed at the connecting parts between the connecting channel 150 and the other flow channels, and the inlet and outlet of the target fluid. When a certain amount of the target fluid flows through the valve 111, the processor enables the valve 111 to close. The predetermined relative proportion of the target bioparticle can be set in the processor 10. When the detection result of the detection area B does not match the predetermined relative proportion of the target bioparticle, the processor 10 closes the valves 111, 131, and opens the valves 112, 132, such that the fluid containing the target bioparticles 900, 1000 can be re-screened by the microelectrode set 700. When the detection result of the detection area B matches the predetermined relative proportion of the target bioparticles 900, 1000, the processor 10 closes the valve 132, and opens the valve 131, such that the fluid having the target bioparticles 900, 1000 reaching the predetermined relative proportion flows away for the follow-up detection. It is noteworthy that the tagged molecules bound to the target bioparticles 900, 1000 in the preceding process are repeatedly irradiated by light in the recycling process. If the tagging is performed by fluorescent labels, it may cause photo-bleaching because of the repeated excitation, such that the detection result may be affected. On the other hand, using the Raman barcode bead 200 of the present invention may avoid the above drawback effectively so as to rapidly and accurately screen the target fluid.

In the above embodiment, the microelectrode set 700 may be formed of conductive materials such as Au, Cu, Ti, Cr, and the like. According to the practical requirement, such as capturing or screening, the shape of the microelectrode set 700 may be designed based on the actual needs, and shall not be limited to the rectangularity mentioned in FIG. 6 to FIG. 9. For example, the shape of unilateral electrode or bilateral electrodes of the microelectrode set 700 formed of a pair of electrodes may be the comb-shaped electrodes, interdigitated electrodes, planar electrodes, and so on.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A microfluidic biosensing system, comprising:
   a processor, storing a Raman barcode database corresponding to at least one Raman spectrum signal;
   a plurality of Raman barcode beads, mixed with a target fluid and coupled to at least one target bioparticle in the target fluid;
   a microfluidic channel, defining a path allowing the target fluid mixed with the plurality of Raman barcode beads to flow therethrough;
   a light source, disposed on the microfluidic channel and generating a beam of light; and
   a spectral detection device, connected to the processor and disposed corresponding to the light source, the spectral detection device receiving the at least one Raman spectrum signal generated when the at least one target bioparticle coupled with the Raman barcode beads is irradiated by the light generated from the light source, and transferring the received at least one Raman spectrum signal to the processor,
   wherein the processor determines a type or types of the at least one target bioparticle by matching the at least one Raman spectrum signals to the Raman barcode database, and calculates a number of the at least one bioparticle of each type according to determination results of each time the Raman barcode spectrum signal is received and transferred by the spectral detection device;
   wherein an optical intensity threshold value is set in the spectral detection device and is adjusted based on the Raman spectrum signal emitted by the Raman barcode beads when just the Raman barcode beads flow through the detection area without binding to the target bioparticle, and the at least one Raman spectrum is valid only when an optical intensity of the at least one Raman spectrum signal at a predetermined wavenumber is greater than the optical intensity threshold value,
   wherein the microfluidic flow channel is split into a first split channel and a second split channel at an end of the microfluidic flow channel, and the microfluidic biosensing system further comprises a microelectrode set, disposed near where the microfluidic flow channel is split and connected to the processor, the processor controlling the microelectrode set generates an electric field to guide the at least one target bioparticle to move toward the first split channel or the second split channel, and
   wherein the light source and the spectral detection device are disposed relatively before the microelectrode set in a flow direction of the target fluid.

2. The microfluidic biosensing system of claim 1, wherein the at least one Raman barcode bead comprises:
   a Raman reporter;
   a Raman enhancer, coupled to the Raman reporter;
   a protective shell, covering the Raman reporter and the Raman enhancer; and
   a biorecognition element, disposed outside the protective shell, the biorecognition element corresponding to the at least one target bioparticle to couple the at least one Raman barcode bead to the at least one target bioparticle.

3. The microfluidic biosensing system of claim 2, wherein the Raman enhancer is a single metal nanoparticle or a nanoaggregate of metal nanoparticles.

4. The microfluidic biosensing system of claim 1, further comprising:
   a sheath flow channel, disposed on the microfluidic channel and providing a sheath flow to the target fluid mixed with the Raman barcode bead before the target fluid is irradiated by the light generated from the light source.

5. The microfluidic biosensing system of claim 1, further comprising:
   a light intensity detector, connected to the processor and disposed corresponding to the light source, the light intensity detector receiving an elastic scattering light signal generated when the at least one target bioparticle of the target fluid is irradiated by the light generated from the light source, and transferring the received elastic scattering light signal to the processor,
   wherein the processor determines a passing timing when the at least one target bioparticle is irradiated by the light generated from the light source according to the elastic scattering light signal.

6. The microfluidic biosensing system of claim 1, further comprising:
   a microelectrode set, disposed corresponding to the light source to generate an electric field to capture the at least one target bioparticle when the at least one target bioparticle is irradiated by the light generated from the light source.

7. The microfluidic biosensing system of claim 1, wherein the microelectrode set is disposed on the first split channel.

* * * * *